United States Patent
Gaylord

[19]

[11] Patent Number: 5,928,172
[45] Date of Patent: Jul. 27, 1999

[54] WRIST BRACE WITH THUMB STRAP

[75] Inventor: Eric L. Gaylord, Charlotte, N.C.

[73] Assignee: Medical Specialties, Inc., Charlotte, N.C.

[21] Appl. No.: 09/033,637

[22] Filed: Mar. 3, 1998

[51] Int. Cl.$^6$ .................................................. A61F 5/00
[52] U.S. Cl. ............................................. 602/21; 602/64
[58] Field of Search ................................ 602/20, 21, 61, 602/62, 64

[56] References Cited

U.S. PATENT DOCUMENTS

| | | |
|---|---|---|
| Re. 32,566 | 12/1987 | Patton . |
| 2,388,330 | 11/1945 | Jungmann . |
| 3,512,776 | 5/1970 | Thomas, Sr. .............................. 602/21 |
| 4,047,250 | 9/1977 | Norman . |
| 4,190,906 | 3/1980 | Patton . |
| 4,438,532 | 3/1984 | Campanella et al. . |
| 4,584,993 | 4/1986 | Nelson ..................................... 602/21 |
| 4,658,441 | 4/1987 | Smith . |
| 4,883,073 | 11/1989 | Aziz ......................................... 602/21 |
| 5,014,689 | 5/1991 | Meunchen et al. . |
| 5,313,667 | 5/1994 | Levine . |
| 5,376,066 | 12/1994 | Phillips et al. . |
| 5,397,296 | 3/1995 | Sydor et al. . |
| 5,415,624 | 5/1995 | Williams .................................. 602/21 |
| 5,513,657 | 5/1996 | Nelson . |
| 5,538,501 | 7/1996 | Caswell . |
| 5,713,837 | 2/1998 | Grim et al. ............................ 602/21 X |

*Primary Examiner*—Linda C. M. Dvorak
*Attorney, Agent, or Firm*—Kennedy, Covington, Lobdell, & Hickmans LLP

[57] ABSTRACT

A wrist brace including a body member which has a dorsal for positioning adjacent the dorsal side of a user's wrist and a palmar portion for positioning adjacent the palmar side of the user's wrist, with the dorsal having a dorsal fastening surface of a predetermined size. A wrist strap is provided for encircling the wrist of the user, and the wrist strap has a fixed end fixed to the body member and a free end for positioning about the user's wrist. An arrangement for releasably fastening the free end of the wrist strap about the user's wrist is also provided. A first thumb strap has a fixed end attached to the palmar portion and a first distal end, while a second thumb strap has a fixed end attached to the palmar portion and a second distal end, and the first and second distal ends are joined together at a joined end. The first and second thumb straps define an opening therebetween for receiving the thumb of the user. The joined end has a joined end fastening surface for releasable fastening to the dorsal fastening surface, with the joined end fastening surface being relatively smaller in size than the dorsal fastening surface, and the joined end fastening surface is adjustably positionable on the dorsal fastening surface so as to provide greater or lesser relative tension on the first and second thumb straps around the thumb of the user.

25 Claims, 9 Drawing Sheets

WRIST BRACE WITH THUMB STRAP

BACKGROUND OF THE INVENTION

The present invention relates generally to wrist braces and, more particularly, to a wrist brace having a thumb strap for supporting areas of the hand and wrist to prevent injury and/or the development of harmful physical conditions.

In recent years, an increased awareness has developed of the harmful effects caused by repetitive strain injuries (RSI) to a large portion of the population. Such RSI's can develop from over use of the hand, wrist, and arm by individuals in a wide variety of occupations, including many office and clerical jobs, construction work, assembly-line, production and many others. RSI's can cause significant pain, and can also result in numbness and reduce the ability to control the hands. Effects of this type can severely diminish the quality of life and productivity of an individual suffering from an RSI.

RSI's which affect the wrist and hand are typically caused by performance of tasks which require the wrist and fingers to be repeatedly bent over and over again. Two well-known types of RSI can occur in the wrist area. The first is Carpal tunnel syndrome, which results from excessive bending of the wrist causing the swelling of tendons in the carpal tunnel, which in turn causes compression of the median nerve as it passes through the carpal tunnel, a narrow passageway on the palmar side of the hand. De Quervain's Disease, one of the other common tendon disorders of the hand, is another type of RSI which develops when the tendons on the radial side of the wrist and the base of the thumb become irritated from repetitive bending of the wrist.

In order to treat or prevent RSI's affecting the wrist and hand, a number of wrist braces and hand braces have been developed. The glove disclosed in Phillips U.S. Pat. No. 5,376,066, for example, is intended to treat or prevent the occurrence of carpal tunnel syndrome by applying a compressive force to the palm, which in turn compresses the carpal tunnel, making the median nerve extending therethrough less vulnerable to injury or strain. The hand brace of Meunchen, et. al. U.S. Pat. No. 5,014,689 is intended to reduce the adverse impact of carpal tunnel syndrome by limiting the range of movement of the hand relative to the wrist, and reduces the effects of De Quervain's condition by providing compression over the base of the thumb, known as the Thenar region.

Known wrist and hand braces, however, suffer from a variety of disadvantages, in that such braces are typically not capable of adequate adjustment to fit a wide variety of individuals, since hand size and shape can vary enormously from person to person. As a result, the brace may not provide sufficient support or compression to fulfill its intended purpose, or may also interfere with the wearer's use of his or her hands to accomplish necessary and/or productive work. Likewise, conventional braces are typically not sufficiently adjustable to provide comfort to a wide variety of individuals. In addition, known wrist and hand braces do not provide for ambidextrous fit on the right or left hand in such a way that maintains the beneficial characteristics of the brace when worn on either hand.

In accordance with the present invention, a wrist brace with a thumb strap is provided which permits adjustment while maintaining its effectiveness and comfort, thereby permitting it to be usefully worn by a wide variety of individuals.

SUMMARY OF THE INVENTION

In accordance with the present invention, a wrist brace is provided for supporting the wrist and adjacent areas to prevent and remedy injury thereto. The wrist brace of the present invention comprises a body member which has a dorsal portion for positioning adjacent the dorsal side of a user's wrist and a palmar portion for positioning adjacent the palmar side of the user's wrist, and the dorsal has a dorsal fastening surface of a predetermined size. A wrist strap is provided for encircling the wrist of the user, and the wrist strap has a fixed end fixed to the body member and a free end for positioning about the user's wrist, while an arrangement for releasable fastening is provided for fastening the free end of the wrist strap about the user's wrist.

A first thumb strap has a fixed end attached to the palmar portion and a first distal end, and a second thumb strap has a fixed end attached to the palmar portion and a second distal end, in the first and second distal ends of the thumb straps are joined together at a joined end. The first and second thumb straps define an opening there between for receiving the thumb of the user. The joined end has an end fastening surface for releasable fastening to the dorsal fastening surface, with the end fastening surface being relatively smaller in size than the dorsal fastening surface so that it can be adjustably positioned on the dorsal fastening surface to provide greater or lesser relative tension on the first and second thumb straps around the thumb of the user.

The wrist brace may be configured to be positionable on the right or left wrist of the user and include a first dorsal fastening surface, a second dorsal fastening surface, a first joined end position fastening surface and a second joined end position fastening surface. The first joined end position fastening surface is for releasable fastening to one of the dorsal fastening surfaces when the wrist brace is on one of the right or left wrists of the user, and the second joined end fastening surface is for releasable fastening to the other of said dorsal fastening surfaces when the wrist brace is on the other of the right or left wrist of the user.

The joined end may have two opposed faces, and the first joined end fastening surface may be on one of the faces and the second joined end fastening surface may be on the other of the faces.

The wrist brace may preferably further include a cover tab foldably connected to the joined end, the cover tab having two opposed faces each having a tab fastening surface for releasable fastening to a corresponding one of the joined end fastening surfaces, whereby when one of the joined end fastening surfaces is releasably fastened to one of the dorsal fastening surfaces, the cover tab is positionable to releasably cover the other of the joined end fastening surfaces.

In a further preferred embodiment, the cover tab may be foldably connected to the joined end by a hinge, and the hinge may define a spacing separating each of the joined end fastening surfaces from the corresponding tab fastening surface. The flexible hinge may be neoprene rubber.

The joined end fastening surfaces, the tab fastening surfaces, and the dorsal fastening surfaces, may include cooperating hook and loop fastener materials. In a preferred embodiment, the joined end fastening surfaces may include hook fastener material, and the tab fastening surfaces may include loop fastener material.

The dorsal of the wrist brace preferably includes a dorsal pocket and a dorsal stay for removable positioning in the pocket. The dorsal stay may have an ulnar edge for positioning adjacent the ulnar side of the user's wrist, with the ulnar edge having a scalloped profile configured to accommodate the distal head of the ulna of the user.

The wrist brace may also include a palmar portion which includes a palmar pocket and a palmar stay for removable positioning in the pocket. The palmar portion may have a first face selectively positionable in an outward orientation about one of the user's wrist, and a second face selectively positionable in an outward orientation about the other of the user's wrist, with each of the palmar portion faces including a palmar pocket and a palmar stay for selective removable positioning in either of the palmar pockets, so that the palmar stay can be positioned so as to provide wearing comfort for the user.

Accordingly, the present invention provides a wrist brace which can be easily and conveniently adjusted to enhance the user's comfort, yet provides support for preventing and treating wrist injuries. Moreover, the wrist brace of the present invention can be configured for wearing on either of the user's wrists in comfort.

DETAILED DESCRIPTION OF THE PREFERRED EMBODIMENT

Figure 1:
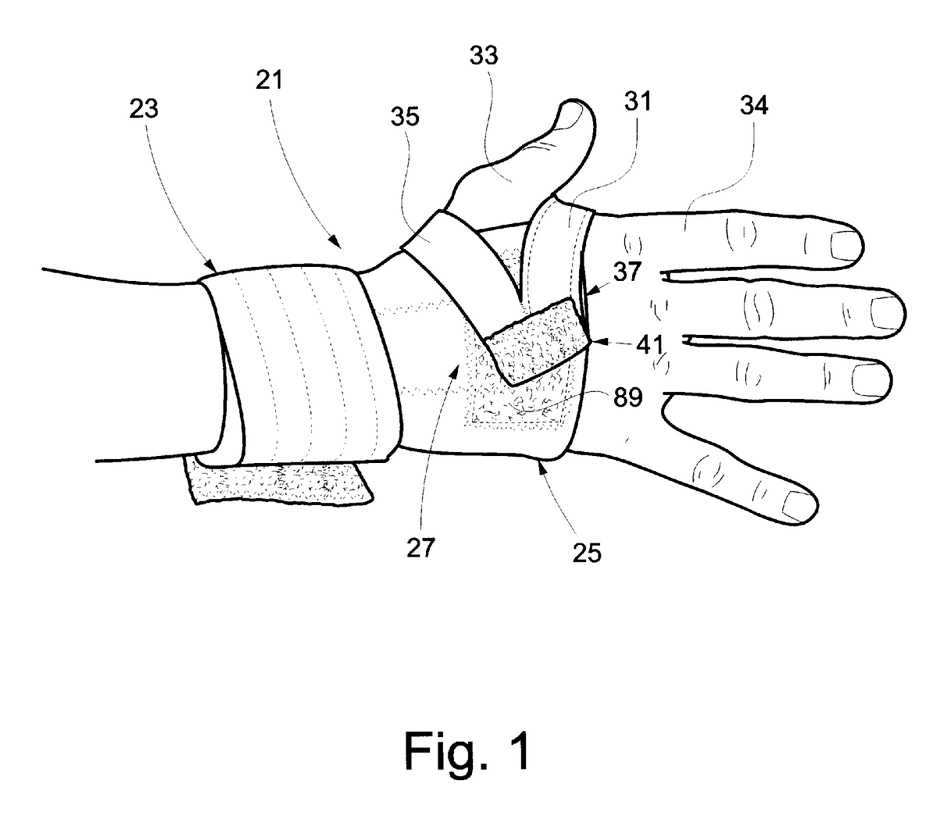
FIG. 1 is a perspective view illustrating the wrist brace of the present invention installed on the right hand and wrist of the user.

Looking now in greater detail at the accompanying drawings, FIG. 1 illustrates a wrist brace 21 of the present invention installed on the right hand and wrist of a user. The wrist strap 23 is attached to a body member 25, which includes a dorsal 27 in position adjacent the dorsal of the user's hand, and a palmar portion 29 (see FIG. 2) positioned adjacent to the palmar portion of the user's hand. A first thumb strap 31 is attached to the palmar portion 29 and, when installed, extends between a thumb 33 and index finger 34 of the user. A second thumb strap 35 extends from the palmar portion 29 around the thumb and is joined to the first thumb strap 31 at a joined end 37. The joined end 37 is releasably attached to the dorsal 29 by an arrangement which will be described in detail presently. A cover tab 41 is shown in its covering disposition covering the joined end 37.

The body member 25 and the first and second thumb straps 31, 35 are preferably fabricated from a material stretchable in all directions, such as a sheet of neoprene rubber which is covered by nylon fabric on both sides. It will be understood that many other materials, such as fabrics, leather, plastics, or the like, may be employed to form the body member 25 and the thumb straps 31, 35 without departing from the scope of the present invention. When in place on the wrist of the user, the wrist brace 21 supports the wrist of the user in a relatively neutral position, and restrains extreme bending motion of the wrist, while also providing a degree of compression on the wrist and hand. In this way, the wrist brace 21 assists in preventing the development of repetitive stress injuries to the wrist and hand, such as carpal tunnel syndrome, De Quervain's Disease, and others. Such injuries typically are caused by repetitive bending of the wrist and/or thumb, which damage the tendons and/or nerves in the hand, as is well known.

By limiting the bending movement of the wrist of the user, the wrist brace 21 can prevent the development of such debilitating repetitive stress injuries. However, as a result of the stretchable nature of the body member 25 and the thumb straps 31, 35, the wrist brace 21 allows for some flexibility to enable the user to undertake and accomplish productive tasks. In addition, the wrist brace 21 provides compression force on the hand and wrist of the user, which aids in the treatment of tendonitis, including the aforementioned De Quervain's Disease. The wrist brace 21 of the present invention provides these benefits along with highly adjustable fit and variation of the compression forces applied to the users hand, while also permitting the same wrist brace 21 to be worn on either the right or left hand, all as will be described presently.

Figure 2:
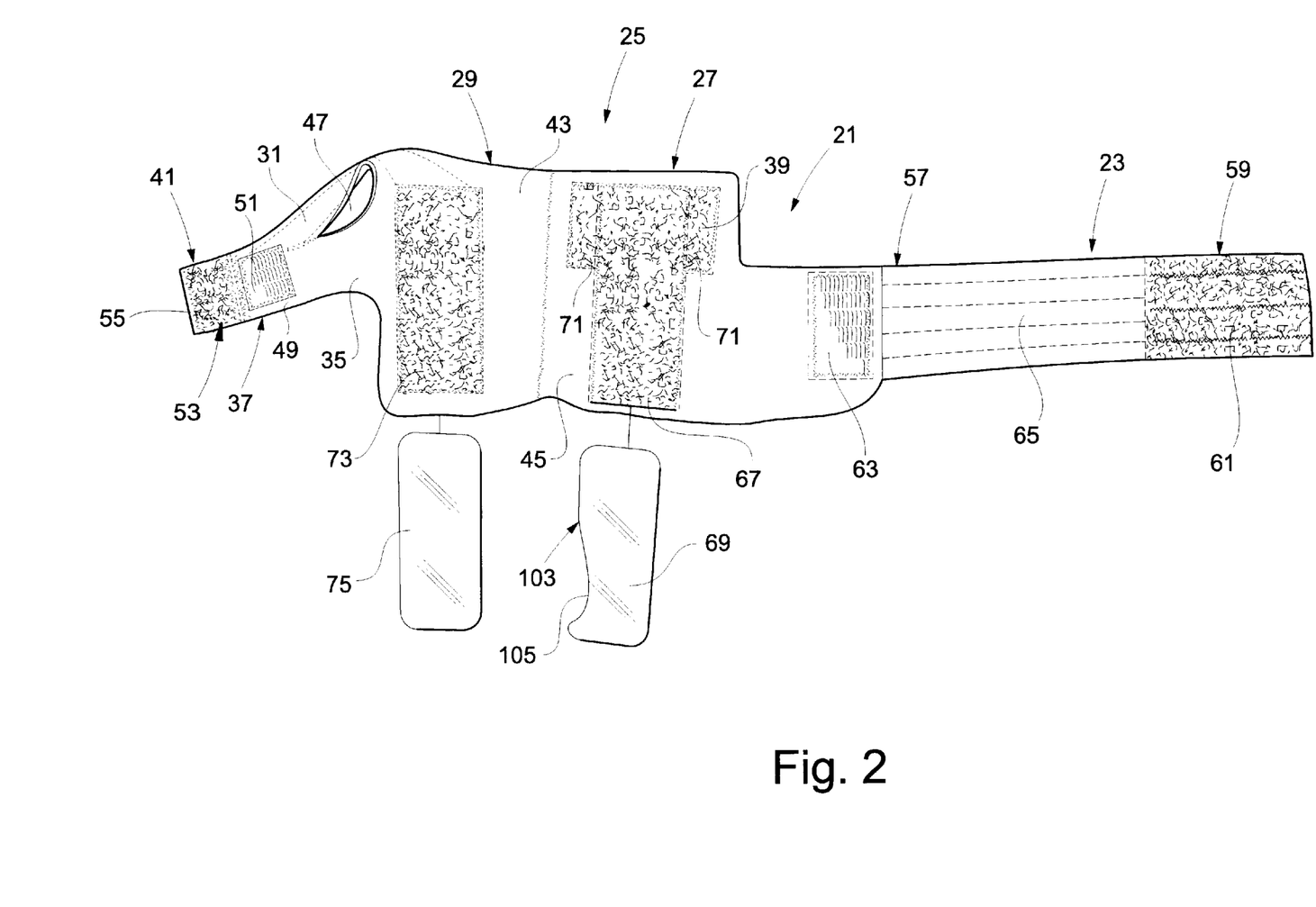
FIG. 2 is a plan view of one face of the wrist brace of the present invention.

The components of the wrist brace 21 of the invention are illustrated particularly in FIG. 2, which shows a first palmar portion face 43 and a first dorsal face 45. The first thumb strap 31 and the second thumb strap 35 are attached to the palmar portion 29 and define an opening 47 through which the user can insert his or her thumb. A first dorsal fastening surface 39 is located in the first dorsal face 45. The joined end 37 which joins the thumb straps 31, 35 has a first joined end face 49, and a first joined end fastening surface 51 is located thereon. The cover tab 41 has a first cover tab face 53 on which a first tab fastening surface 55 is formed.

The wrist strap 23 has a fixed end 57 attached to the dorsal 27 and a free end 59. A first free end fastening surface 61 is formed on the free end 59, while a first closure fastening surface 63 is formed on the first face 45 of the dorsal 27. The wrist strap 29 also includes an elastic portion 65 to provide for a snug and comfortable fit of the wrist strap 23 around the wrist of the user.

A dorsal pocket 67 is located on the first dorsal face 45 for receiving a dorsal stay 69, which is preferably formed from polyethylene material. The first dorsal fastening surface 39 is contiguous with the first dorsal pocket 67 on the first dorsal face 45, and is formed to have a substantially larger surface area than the first joined end fastening surface 51 for a purpose that will be described presently. The first dorsal fastening surface 71 and the dorsal pocket 67 are stitched together at seams 71 in the illustrated embodiment of the invention. A first palmar pocket 73 is formed on the first palmar portion of phase 43 to receive a palmar stay 75 which is also preferably formed from polyethylene material.

Figure 3:
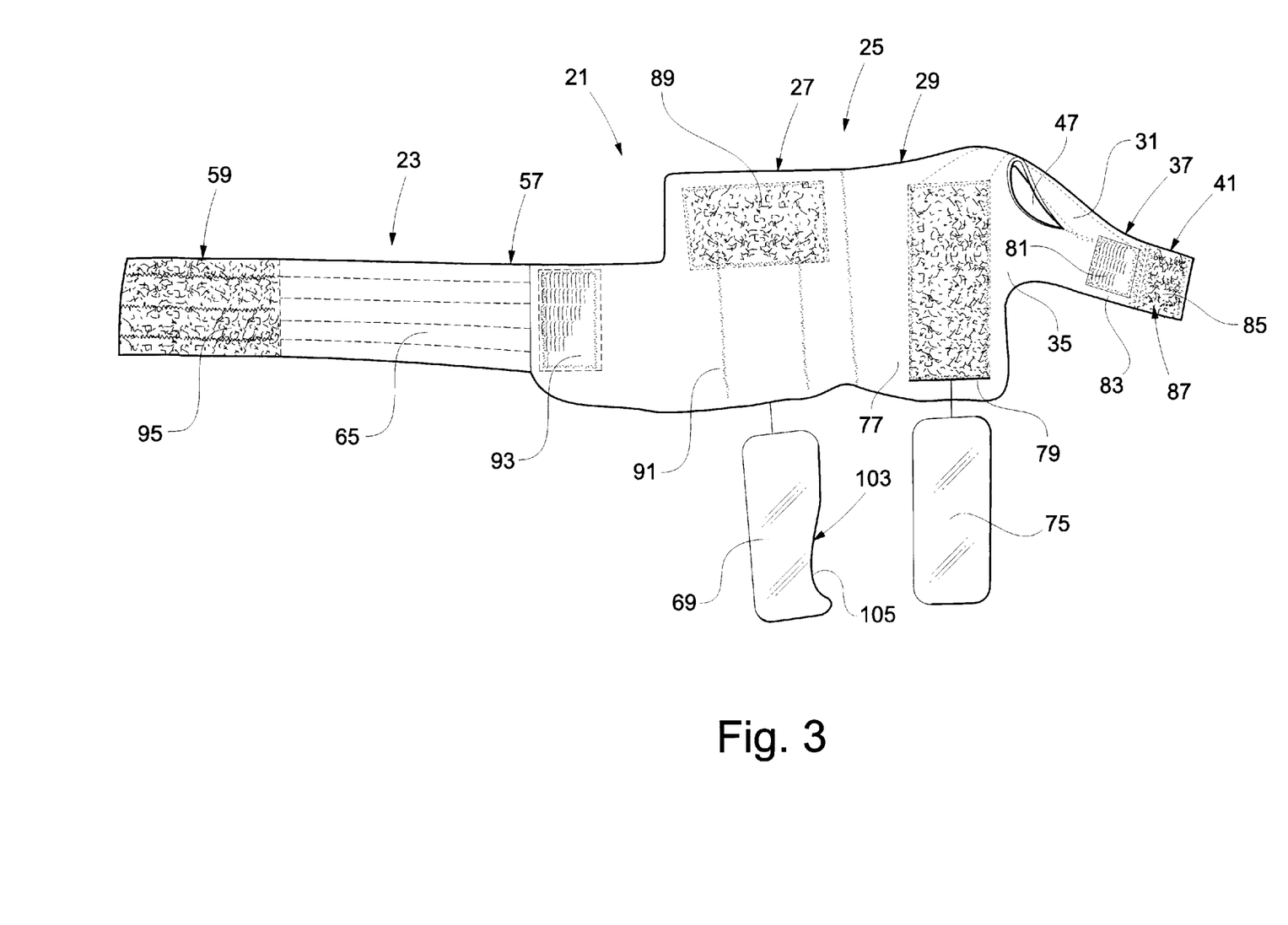
FIG. 3 is a plan view of a face of the wrist brace of the present invention opposite to that shown in FIG. 2.

FIG. 3 illustrates the opposed side of the wrist brace 21 oriented so that a user can place the palm of his or her left hand on a second palmar portion face 77 with his or her thumb in the thumb opening 47 for attachment of the wrist brace 21 around his or her left hand and wrist. A second palmar pocket 79 is located on the second palmar portion face 77 for receiving the palmar stay 75. Typically, the palmar stay 75 will be positioned in the palmar pocket 73, 79 which is oriented outwardly or most distant from the palm of the user, to provide enhanced comfort for the user.

A second joined end fastening surface 81 is located on a second joined end face 83, and a second cover tab fastening surface 85 is located on a second cover tab face 87. A second dorsal fastening surface 89 is located on a second dorsal face 91, while a second closure fastening surface is also located on the second dorsal face adjacent the fixed end 57 of the wrist strap 23. The second free end fastening surface is located at the free end 59 of the wrist strap 23.

The various fastening surfaces of the wrist strap 21 are preferably formed from hook and loop fastening material such as VELCRO®, which is available through Velcro Industries of the Netherlands. Preferably, the joined end fastening surfaces 51, 81 are formed from hook fastener material, while the cover tab fastening surfaces 55, 85 and the dorsal fastening surfaces 39,89 are formed from loop fastener material on the wrist strap 23, the free end fastening surfaces 61, 95 are advantageously formed from loop fastener material, and the closure fastening surfaces 63, 93 are advantageously formed from hook fastener material. It will be understood that other releasable fasteners, such as snaps, hook and eyes, buckles, and the like, could be used on the fastening surfaces of the wrist brace 21, including the wrist strap 23, without departing from the scope of the present invention.

Figure 4:
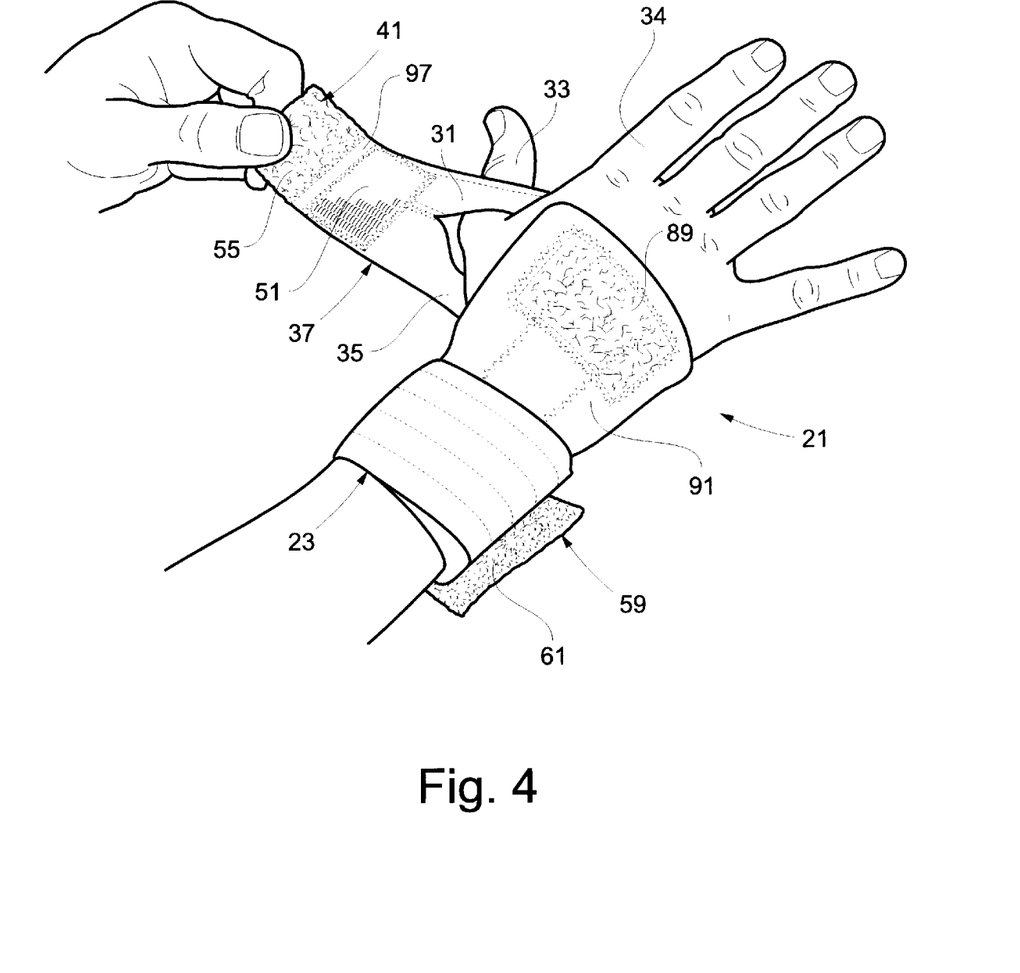
FIG. 4 is a perspective view illustrating the wrist brace of the present invention partially installed on a person's right hand and wrist.

FIG. 4 illustrates the wrist brace 21 of the present invention in the last stages of installation on the right hand and wrist of a user. The wrist brace 21 would be initially positioned generally as shown in FIG. 2 with the user placing his or her palm on the first palmar portion face 45 with his or her thumb passing through the thumb opening 47. It will be understood that in illustrations of the wrist brace 21 as installed on the hand of the user, certain items may be hidden from view by the brace 21. However, reference can be made to FIGS. 2 and 3, in particular, to see the location of those items. As seen in FIG. 4, the wrist strap 23 has been secured about the wrist of the user and releasably fastened in place by bringing the first free end fastening surface 61 in fastening contact with the second closure fastening surface 93 so that the wrist strap 23 comfortably yet firmly encircles the wrist of the user. In order to assist closure of the wrist brace 23 about the wrist of the user, the first closure fastening surface 63 is also releasably fastened to the surface of the second palmar pocket 79, which consists of loop material that is releasably fastenable to the hook material of the first closure fastening surface 63.

By positioning the wrist brace 21 in the above-described manner, the first dorsal face 45 is brought into contact with the dorsal of the user's hand. The first and second thumb straps 31, 35 then extend around the thumb of the user and meet at the joined end 37. In the position shown in FIG. 4, the user is preparing to releasably fasten the first joined end fastening surface 51 to the second dorsal fastening surface 89. As noted above, the first joined end fastening surface 51 is substantially smaller in surface area than the second dorsal fastening surface 89, so that the joined end fastening surface 51 can be releasably fastened in a number of different positions on the second dorsal fastening surface 89 to adjust the fit of the first and second thumb straps 31, 35, as will be discussed presently in more detail in connection with FIG. 6. The cover tab 41 is foldably connected to the joined end 37 by a flexible hinge 97, which is preferably formed from neoprene rubber faced with nylon fabric, the same material from which the body member 25 is preferably formed. It will be understood that other flexible materials, such as fabric, leather, plastics, or the like, may be employed to form the flexible hinge 97.

Figure 5:
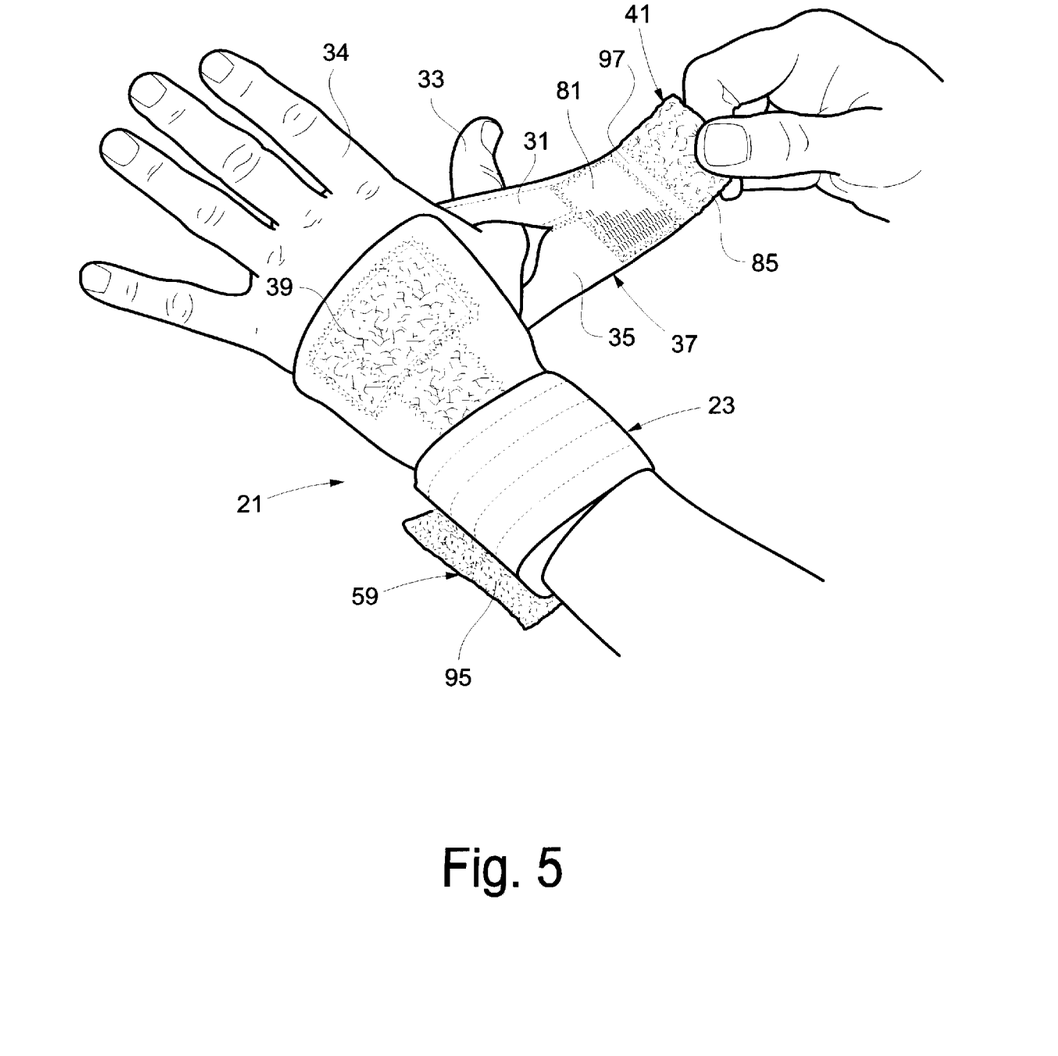
FIG. 5 is a perspective view illustrating the wrist brace of the present invention partially installed on the left hand and wrist of a user.

In FIG. 5, the wrist brace 21 of the present invention is seen in the last stages of installation on the left hand and wrist of a user. The wrist brace 21 was first positioned generally as shown in FIG. 3, with the user placing his or her left palm on the second palmar portion face 77 with the user's thumb passing through the thumb opening 47. The wrist strap is shown in FIG. 5 positioned around the left wrist of the user with the second free end fastening surface 95 releasably fastened to the first closure fastening surface 63, and the second closure fastening surface 93 releasably fastened to the first palmar pocket 73. The second dorsal face 91 is positioned next to the dorsal of the user's left hand, and the second joined end fastening surface 81 is positioned in preparation for attachment to the first dorsal fastening surface 39, in the same general manner as described above in connection with FIG. 4. It can thus be seen that the wrist brace 21 of the present invention can be advantageously worn on either the right or left hand and wrist of the user, while maintaining all the advantages of it's flexibility in adjustment, fit and convenience.

Figure 6:
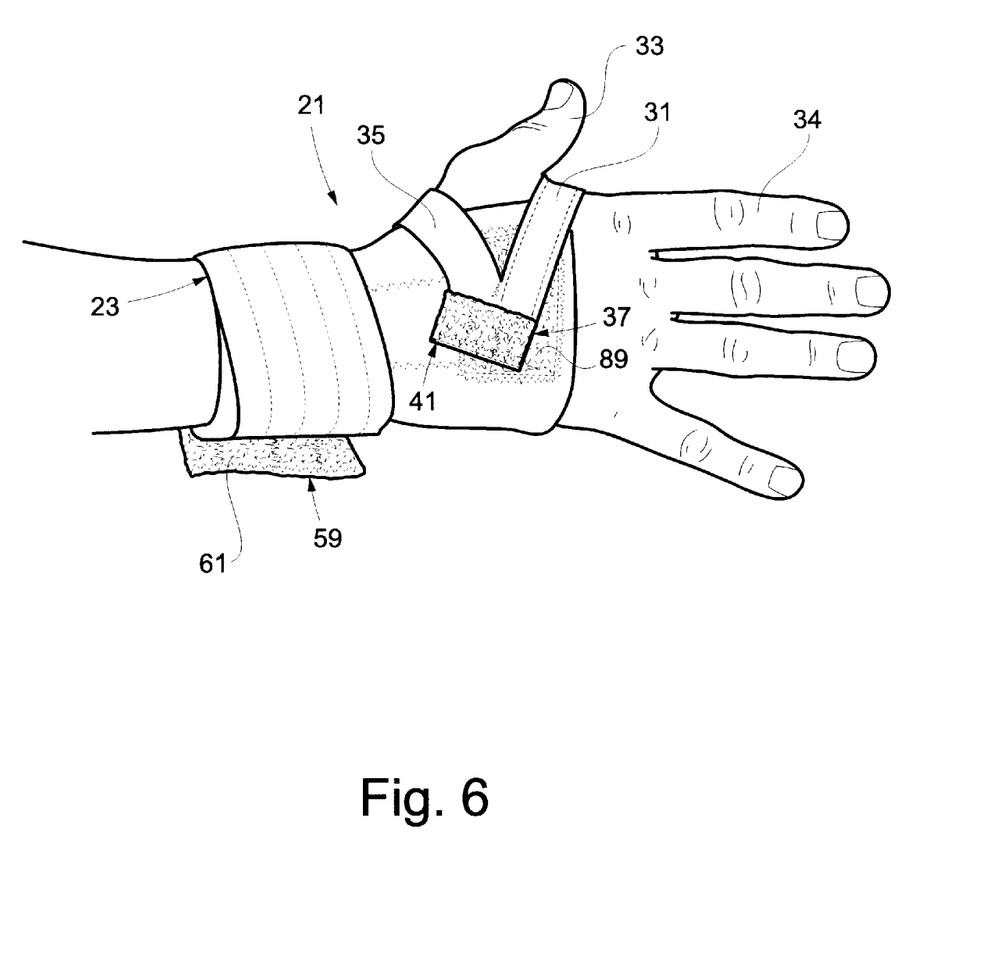
FIG. 6 is a perspective view similar to FIG. 1, with a joined end adjustably positioned on a dorsal fastening surface of the present invention.

The adjustable positioning of the first joined end fastening surface 51 on the second dorsal fastening surface 89 is illustrated in FIGS. 1 and 6, which depict two of the many options available in customizing the fit of the wrist brace 21 of the present invention. As noted above, the dorsal fastening surfaces 39, 89 are substantially larger in surface area than the respective joined end fastening surfaces 51, 81, which allows the joined end 37 to be positioned in a wide variety of locations to produce different degrees of tension in the first and second thumb straps 31, 35, in turn producing different levels of compression force applied to the areas surrounding the thumb of the user. For example, in FIG. 1 the first joined end fastening surface 51 is releasably fastened to the second dorsal fastening surface 89 so that the joined end portion 37 is positioned in a location relatively close to the fingers of the user, but generally midway between the radial and ulnar sides of the hand. Such an orientation would be likely to create a moderate degree of tension in the second thumb strap 35, thereby applying pressure to the base of the thumb of the user. In such a configuration, a lesser degree of tension would generally be applied to the first thumb strap 31, resulting in lesser force applied to the area between the thumb 33 and the index finger 34 of the user.

In contrast, FIG. 6 illustrates the joined end portion 37 in a different position as a result of the first joined end fastening surface 51 being releasably fastened to the second dorsal fastening surface 89 in a position relatively closer to the wrist of the user, and somewhat relatively closer to the ulnar side of the user's wrist. In this configuration, a relatively higher amount of tension would generally be applied to the first thumb strap 31, resulting in a relatively higher degree of compression force being applied to the area between the thumb 33 and index finger 34 of the user. A moderate degree of tension would generally be applied to the second thumb strap 35 in such configuration.

It will be understood that this arrangement allows the joined end 37 to be selectively positioned so as to produce numerous combinations of tension on the thumb straps 31, 35, thereby permitting the user to selectively adjust the resulting compression force applied to the area surrounding his or her thumb 33. This high degree of adjustability allows the user to provide the desired amount of restraint to movement of the thumb, thus advantageously preventing development of De Quervain's Disease and also assisting in treatment of this condition. It will also be understood that the same adjustable positioning of the joined in 37 is possible when the wrist brace 21 is worn on the left hand and wrist of the user, and can be attained by fastening the second joined end fastening surface 81 in the desired location on the first dorsal fastening surface 45.

Figure 7:
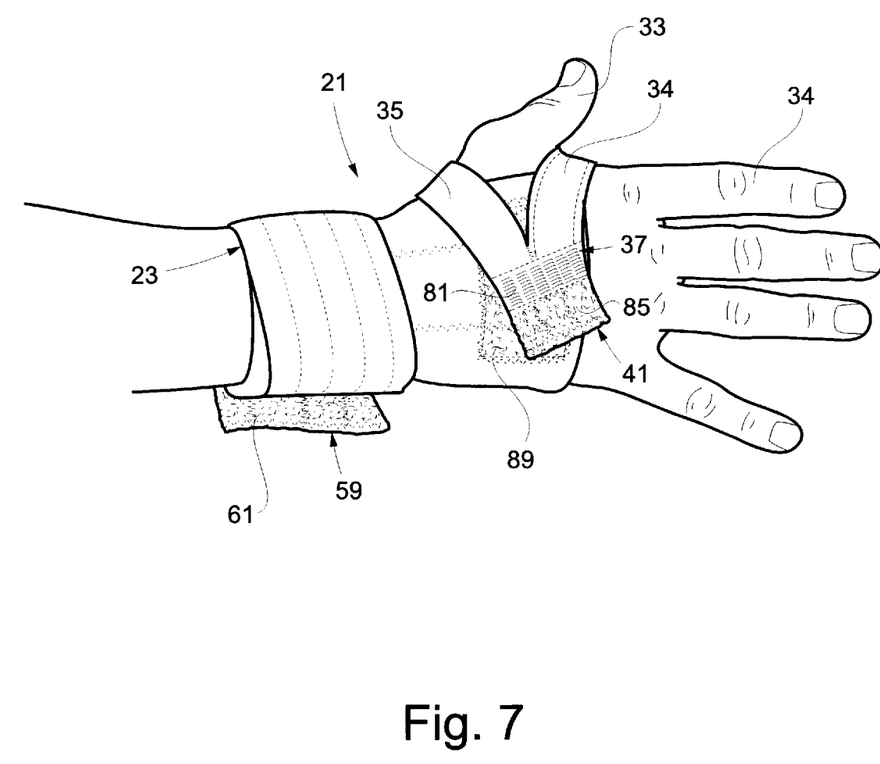
FIG. 7 is a perspective view illustrating the wrist brace of the present invention installed on the right hand and wrist of a user, with a cover tab of the wrist brace prior to being releasably fastened to a joined end fastening surface.

FIG. 7 shows the wrist brace 21 of the present invention with the joined end 37 releasably fastened to the second dorsal fastening surface 89, but with the cover tab 41 not yet positioned in its covering disposition to cover the hook material of the second joined end fastening surface 81. The step of covering the fastening surface 81 can be easily accomplished by folding the flexible hinge 97 (see FIG. 8) so as to bring the second cover tab fastening surface 85 into releasable fastening contact with the second joined end fastening surface 81. The aforementioned hook material of the second joined end fastening surface 81 has a rough texture which, if left exposed, can create serious inconveniences for the user. The hook material can irritate the skin of the user with which it comes into contact, and will also snag threads, lint, and debris, creating an unsightly appearance and ultimately decreasing the fastening effectiveness of the hook and loop fastener material.

The cover tab 41, when in its covering disposition as shown in FIGS. 1 and 6, thus provides a substantial benefit by covering the hook material of the respective joined end fastening surfaces 51, 81 and shielding such hook material from contact with the user, clothing, or other materials. In a preferred embodiment of the present invention, all hook materials of the various fastening surfaces are covered or otherwise shielded from open exposure when installation of the wrist brace 21 is complete.

Figure 8:
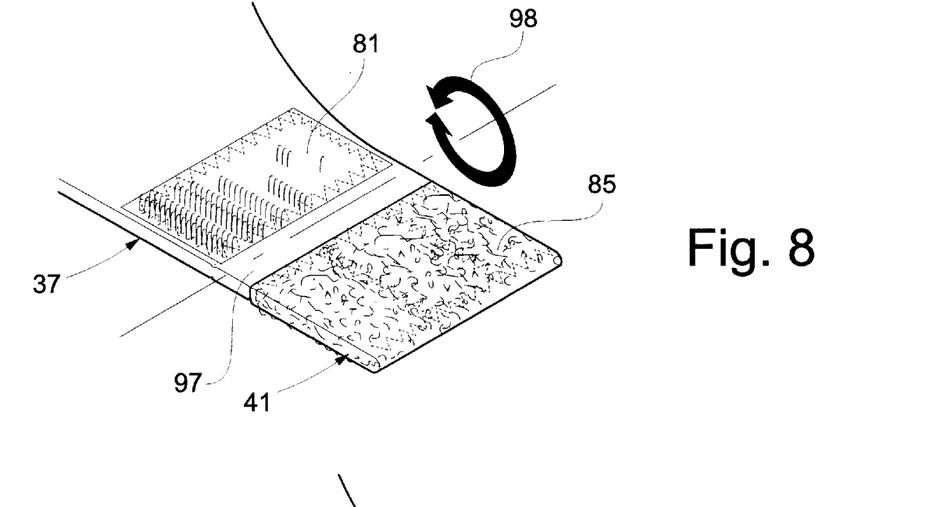
FIG. 8 is a detailed view showing the joined end and cover tab of the wrist brace of the present invention.
Figure 9:
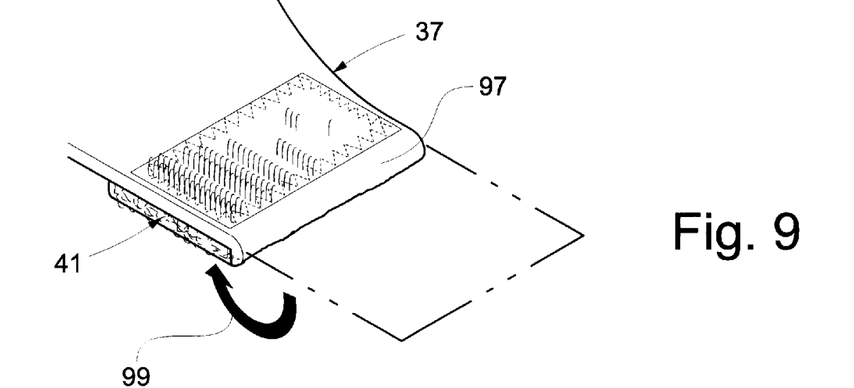
FIG. 9 is a view similar to FIG. 8 showing the cover tab releasably fastened to one side of the joined end.
Figure 10:
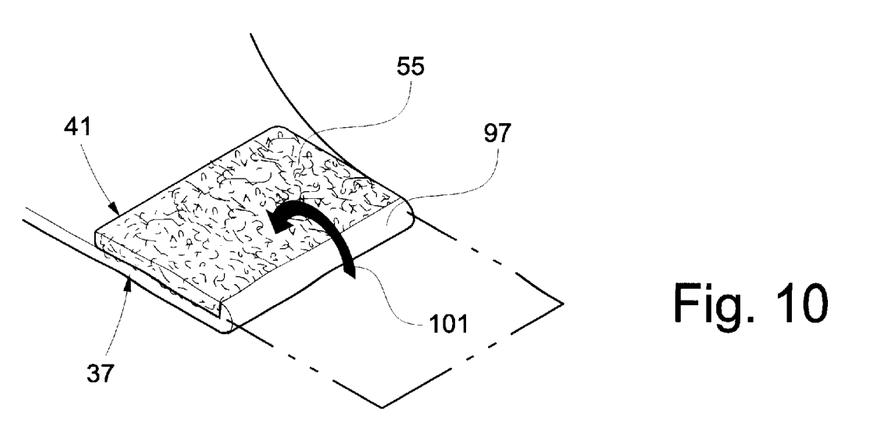
FIG. 10 is a view similar to FIG. 8 showing the cover tab releasably fastened to another side of the joined end.

The flexible hinge 97 is shown in detail in FIGS. 8, 9, and 10. In FIG. 8, the flexible hinge 97 is in its unfolded disposition, and the cover tab 41 is not in its covering disposition. The flexible hinge 97 provides a spacing which separates the second cover tab fastening surface 85 from the second joined end fastening surface 81, and it will be understood that the first cover tab fastening surface 55 and the first joined end fastening surface 51 are likewise separated and spaced from each other by the hinge 97(see FIG. 10). The spacing provided by the hinge 97 allows folding action in the directions shown on arrow 98 to take place within the extent of the hinge 97 without requiring the cover tab fastening surfaces 55, 85 or the joined end fastening surfaces 51, 81 to be substantially bent. By providing a hinge 97 which is flexible and by spacing the cover tab fastening surfaces from the joined end fastening surfaces, the folding action can be reliably confined to the hinge 97, which results in a more consistent folding action. In particular, the hook material is relatively more rigid and not easily folded in a predictable fashion. Thus, the flexible hinge 97 advantageously allows easy and convenient folding of the cover tab 41 to cover the hook material of the joined end fastening surfaces 51, 81.

FIG. 9 shows the cover tab in its covering disposition to cover the first joined end fastening surface 51 after having been moved in the direction shown by the arrow 99. The hinge 97 is in its folded disposition, with the folding action generally confined to the hinge 97. In FIG. 10, the cover tab 41 is in its covering disposition overlaying the second joined end fastening surface 81 following movement in the direction shown by the arrow 101, with the folding action again being generally confined to the hinge 97.

Figure 11:
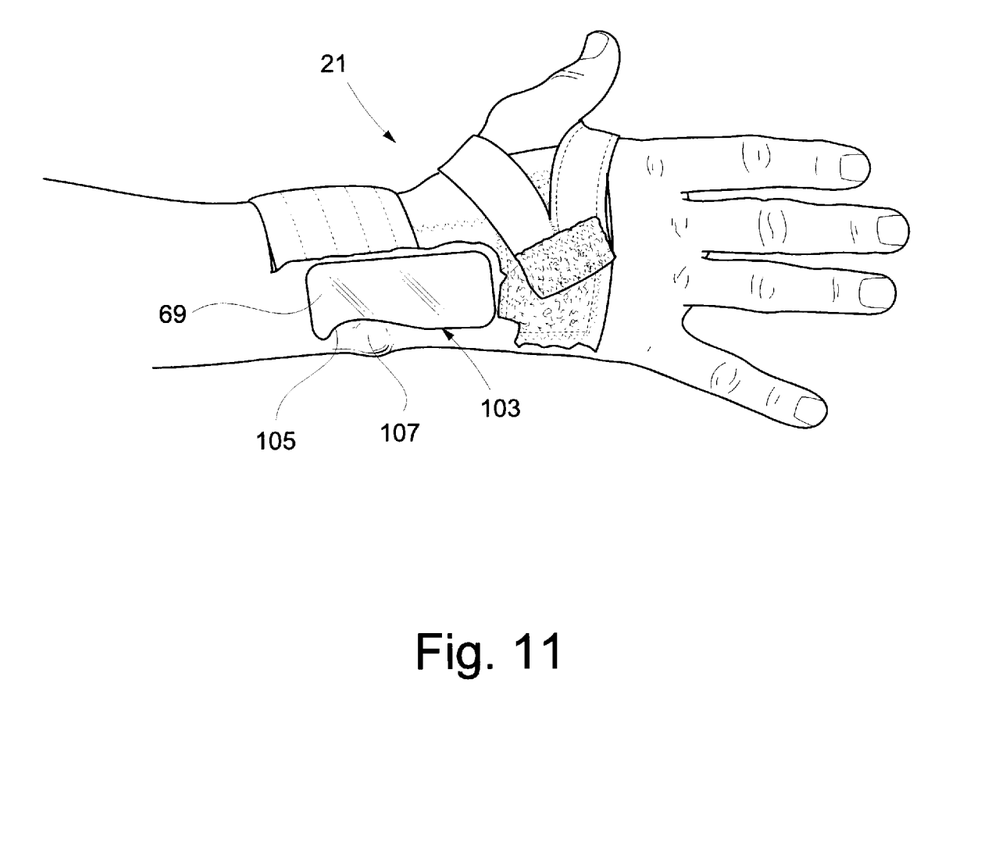
FIG. 11 is a perspective view illustrating the wrist brace of the present invention with a cut away to show a dorsal stay of the wrist brace and the ulna of the user.

FIG. 11 shows the wrist brace 21 of the present invention installed on the right hand and wrist of a user with a portion cut away so that the dorsal stay 69 can be seen. In particular, the dorsal pocket 67 is not depicted so that the dorsal stay 69 can be shown in its desired position and orientation on the hand and wrist of the user. The dorsal stay 69 includes an ulnar edge 103 which has a scalloped profile 105 for accommodating the distal end of the ulna bone 107 of the user, which forms a protruding prominence at the wrist. The scalloped profile 105 thus permits the dorsal stay 69 to be positioned in close relationship to the dorsal of the hand and wrist of the user to provide the desired amount of bending restraint, but accommodates the ulna 107 for a comfortable fit.

The composition of the material forming the dorsal stay 67 and the palmar stay 75 can be varied so as to provide more flexible or more rigid stays 67, 75. Variation of the rigidity of the stays 67, 75 will provide more or less restrainment of bending of the user's wrist. By selecting stays 67, 75 of particular rigidity, the user can customize the wrist brace 21 of the present invention to provide the desired degree of bending restraint.

The wrist brace 21 of the present invention has several advantages over previous hand and wrist braces. The fit of the wrist brace 21 is highly adjustable and the arrangement of the dorsal fastening surfaces and the joined end fastening surfaces allows for customized and precise adjustment of the force applied around both the base of the thumb and the area between the thumb and the index finger of the user. The resulting precision of adjustment provides significant advantages and benefits in protecting and treating the tendons in the area of the thumb and other hand/wrist portions.

The cover tab of the wrist brace of the present invention allows rough hook fastener materials on the exposed joined end fastening surfaces to be covered and therefore prevents contact of the hook material with skin or other materials which will become caught or enmeshed in the hooks. Comfort and appearance of the wrist brace is thereby enhanced. The scalloped profile of the ulnar edge of the dorsal stay also increases the comfort of the wrist brace, while at the same time augmenting the effectiveness of the bending restrain provided by the dorsal stay.

It will therefore be readily understood by those persons skilled in the art that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A wrist brace comprising:

(a) a body member having a dorsal portion for positioning adjacent the dorsal side of a user's wrist and a palmar portion for positioning adjacent to the palmar side of the user's wrist;

(b) said dorsal portion having a dorsal fastening surface of a predetermined size;

a wrist strap for encircling the wrist of the user, said wrist strap having a fixed end fixed to said body member and a free end for positioning about the user's wrist;

(c) means for releasably fastening said free end of said wrist strap about the user's wrist;

(d) a first thumb strap having a fixed end attached to said palmar portion and a first distal end;

(e) a second thumb strap having a fixed end attached to said palmar portion and a second distal end;

(f) a joined end portion at which said first and second distal ends are joined together, said first and second thumb straps defining an opening therebetween for receiving the thumb of the user; and (g) said joined end portion having a joined end portion fastening surface for releasable fastening to said dorsal fastening surface, said joined end portion fastening surface being relatively smaller in size than said dorsal fastening surface, whereby said joined end portion fastening surface is adjustably positionable on said dorsal fastening surface so as to provide greater or lesser relative tension on said first and second thumb straps around the thumb of the user.

2. The wrist brace of claim 1, wherein said wrist strap includes an elastic portion.

3. The wrist brace of claim 1, wherein said means for releasably fastening is cooperating hook and loop fastener materials positioned on said free end and said body member.

4. The wrist brace of claim 1, wherein said joined end portion fastening surface and said dorsal fastening surface include cooperating hook and loop fastener materials.

5. The wrist brace of claim 1, wherein said wrist brace is configured to be positionable on the right or left wrist of the user, and wherein said dorsal fastening surface is a first dorsal fastening surface and said dorsal portion includes a second dorsal fastening surface, said joined end portion fastening surface is a first joined end portion fastening surface and said joined end portion includes a second joined end portion fastening surface, said first joined end portion fastening surface is for releasable fastening to one of said dorsal fastening surfaces when said wrist brace is on one of the right or left wrist of the user, and said second joined end portion is for releasable fastening to the other of said dorsal fastening surfaces when said wrist brace is on the other of the right or left wrist of the user.

6. The wrist brace of claim 5, wherein said joined end portion has two opposed face portions, and said first joined end portion fastening surface is on one of said face portions and said second joined end portion fastening surface is on the other of said face portions.

7. The wrist brace of claim 6, further including a cover tab foldably connected to said joined end portion, said cover tab having two opposed face portions each having a cover tab fastening surface for releasable fastening to a corresponding one of said joined end portion fastening surfaces, whereby when one of said joined end portion fastening surfaces is releasably fastened to one of said dorsal fastening surfaces, said cover tab is positionable to releasably cover the other of said joined end portion fastening surfaces.

8. The wrist brace of claim 7, wherein said cover tab is foldably connected to said joined end portion by a hinge portion, and said hinge portion defines a spacing separating each of said joined end portion fastening surfaces from said corresponding cover tab fastening surface.

9. The wrist brace of claim 8, wherein said hinge portion is neoprene rubber.

10. The wrist brace of claim 7, wherein said joined end portion fastening surfaces, said cover tab fastening surfaces, and said dorsal fastening surfaces include cooperating hook and loop fastener materials.

11. The wrist brace of claim 10, wherein said joined end portion fastening surfaces include hook fastener material, and said cover tab fastening surfaces include loop fastener material.

12. The wrist brace of claim 1, wherein said dorsal portion includes a dorsal pocket and a dorsal stay for removable positioning therein.

13. The wrist brace of claim 12, wherein said dorsal stay has an ulnar edge for positioning adjacent the ulnar side of the user's wrist, said ulnar edge having a scalloped profile configured to accommodate the ulna of the user.

14. The wrist brace of claim 1, wherein said palmar portion includes a palmar pocket and a palmar stay for removable positioning therein.

15. The wrist brace of claim 14, wherein said palmar portion has a first face selectively positionable in an outward orientation about one of the user's wrists, and a second face selectively positionable in an outward orientation about the other of the user's wrists, each of said palmar portion faces including a palmar pocket, and a palmar stay for selective removable positioning in either of said palmar pockets, whereby said palmar stay can be positioned so as to provide wearing comfort for the user.

16. The wrist brace of claim 1, wherein said body member is neoprene rubber.

17. A wrist brace selectively positionable on the right or left wrist of a user, comprising:

(a) a body member having, a dorsal portion for positioning adjacent the dorsal side of either of the user's wrists and a palmar portion for positioning adjacent the palmar side of either of the user's wrists;

(b) said dorsal portion having a first face selectively positionable in an outward orientation about one of the user's wrists, and a second face selectively positionable in an outward orientation about the other of the user's wrists, said dorsal portion further including a first dorsal fastening surface on said first face and a second dorsal fastening surface on said second face;

(c) a wrist strap for encircling the selected wrist of the user, said wrist strap having a fixed end fixed to said body member and a free end for positioning about the selected wrist of the user;

(d) means for releasably fastening said free end of said wrist strap about the selected wrist of the user;

(e) a thumb strap defining an opening for receiving the respective thumb of the user, said thumb strap having a fixed end attached to said palmar portion and a distal end;

(f) said distal end having two opposed face portions each having an end fastening surface for releasable fastening to a corresponding one of said dorsal fastening surfaces to secure said thumb strap about the respective thumb of the user; and (g) a cover tab foldably connected to said distal end, said cover tab having two opposed tab face portions each having a cover tab fastening surface for releasable fastening to a corresponding one of said end fastening surfaces, whereby when one of said end fastening surfaces is releasably fastened to a corresponding one of said dorsal fastening surfaces, said cover tab is positionable to releasably cover the other of said end fastening surfaces.

18. The wrist brace of claim 17, wherein said cover tab is foldably connected to said joined end portion by a flexible hinge portion, and said flexible hinge portion defines a spacing separating each of said joined end portion fastening surfaces from said corresponding tab fastening surface.

19. The wrist brace of claim 18, wherein said hinge portion is neoprene rubber.

20. The wrist brace of claim 17, wherein said joined end portion fastening surfaces, said tab fastening surfaces, and said dorsal fastening surfaces include cooperating hook and loop fastener materials.

21. The wrist brace of claim 20, wherein said joined end portion fastening surfaces include hook fastener material, and said tab fastening surfaces include loop fastener material.

22. The wrist brace of claim 17, wherein said dorsal portion includes a pocket and a dorsal stay for removable positioning therein.

23. The wrist brace of claim 22, wherein said dorsal stay has an ulnar edge for positioning adjacent the ulnar side of the selected wrist of the user, said ulnar edge having a scalloped profile configured to accommodate the ulna at the selected wrist of the user.

24. The wrist brace of claim 17, wherein said palmar portion includes a pocket and a palmar stay for removable positioning therein.

25. The wrist brace of claim 24, wherein said palmar portion has a first face selectively positionable in an outward orientation about one of the user's wrists, and a second face selectively positionable in an outward orientation about the other of the user's wrists, each of said palmar portion faces including a palmar pocket, and a palmar stay for selective removable positioning in either of said palmar pockets, whereby said palmar stay can be positioned so as to provide wearing comfort for the user.

* * * * *